United States Patent
Khan

(10) Patent No.: US 11,801,397 B2
(45) Date of Patent: Oct. 31, 2023

(54) WEARABLE LIGHT THERAPY DEVICE

(71) Applicant: Shining Buddha Corp., Sheridan, WY (US)

(72) Inventor: Rahil (Ray) Khan, Irvine, CA (US)

(73) Assignee: Shining Buddha Corp., Sheridan, WY (US)

( * ) Notice: Subject to any disclaimer, the term of this patent is extended or adjusted under 35 U.S.C. 154(b) by 0 days.

(21) Appl. No.: 17/714,269

(22) Filed: Apr. 6, 2022

(65) Prior Publication Data

US 2022/0323782 A1 Oct. 13, 2022

Related U.S. Application Data

(60) Provisional application No. 63/214,557, filed on Jun. 24, 2021, provisional application No. 63/171,455, filed on Apr. 6, 2021.

(51) Int. Cl.
  *A61N 5/067* (2006.01)
  *A61N 5/06* (2006.01)

(52) U.S. Cl.
  CPC ...... *A61N 5/067* (2021.08); *A61N 2005/0645* (2013.01); *A61N 2005/0651* (2013.01); *A61N 2005/0663* (2013.01)

(58) Field of Classification Search
  CPC ...... A61B 18/20–18/28; A61N 5/06–2005/073
  USPC ..................... 606/2–19; 607/88–94
  See application file for complete search history.

(56) References Cited

U.S. PATENT DOCUMENTS

| | | | |
|---|---|---|---|
| 6,443,978 B1 * | 9/2002 | Zharov | A61N 5/0616 606/2 |
| 11,110,295 B1 | 9/2021 | Truckai et al. | |
| 2005/0197681 A1 * | 9/2005 | Barolet | A61N 5/0616 607/86 |
| 2008/0085265 A1 | 4/2008 | Schneider et al. | |

(Continued)

FOREIGN PATENT DOCUMENTS

| KR | 100889296 | * 3/2009 | ............ A61H 19/00 |
|---|---|---|---|
| WO | 2020077427 A1 | 4/2020 | |

OTHER PUBLICATIONS

Geniole et al., "Is testosterone linked to human aggression? A meta-analytic examination of the relationship between baseline, dynamic, and manipulated testosterone on human aggression", Dec. 28, 2019, Hormones and Behavior, 123: 104644, pp. 1-11 (Year: 2019).*

(Continued)

*Primary Examiner* — Jonathan T Kuo
*Assistant Examiner* — Vynn V Huh
(74) *Attorney, Agent, or Firm* — Umberg Zipser LLP

(57) ABSTRACT

A wearable photobiomodulation device comprises a shell portion and an illumination module and is configured to deliver light to a photoresponsive tissue of an individual. In some embodiments, the illumination module provides red and/or infrared light to a photoresponsive tissue on an individual at a dose of between about 5-50 mJ/cm$^2$ over a target illumination area of about 100-200 cm$^2$. Exemplary devices may be configured as a wearable sports cup with an integral or detachable illumination module that provides effective amounts of light to a target are to so effect photobiomodulation in an individual wearing the device.

9 Claims, 8 Drawing Sheets

(56) References Cited

U.S. PATENT DOCUMENTS

| | | | |
|---|---|---|---|
| 2009/0112294 A1 | 4/2009 | Huang et al. | |
| 2009/0287076 A1 | 11/2009 | Boyden et al. | |
| 2011/0060266 A1* | 3/2011 | Streeter | A61N 5/0613 604/20 |
| 2014/0303693 A1* | 10/2014 | Haarlander | A61N 5/0616 607/91 |
| 2015/0196455 A1 | 7/2015 | Mertens et al. | |
| 2017/0157430 A1 | 6/2017 | Cheatham, III et al. | |
| 2019/0224495 A1* | 7/2019 | Pina | A61N 5/0617 |
| 2020/0368549 A1* | 11/2020 | Stephan | A61F 13/14 |
| 2021/0299464 A1* | 9/2021 | Reign | A61N 5/0613 |

OTHER PUBLICATIONS

Avci et al., "Low-level laser (light) therapy (LLLT) in skin: stimulating, healing, restoring," Semin Cutan Med Surg., Mar. 2013; 32(1): 41-52.

Chung et al., "The Nuts and Bolts of Low-Level Laser (Light) Therapy," Ann Biomed Eng., Feb. 2012; 40(2): 516-533, 29 pages.

Moskvin et al., "Effectiveness of low level laser therapy for treating male infertility," BioMedicine, (ISSN 2211-8039), Jun. 2018, vol. 8, No. 2, Article 7, pp. 1-15.

Wunsch et al., "A Controlled Trial to Determine the Efficacy of Red and Near-Infrared Light Treatment in Patient Satisfaction, Reduction of Fine Lines, Wrinkles, Skin Roughness, and Intradermal Collagen Density Increase," Photomedicine and Laser Surgery, vol. 32, No. 2, 2014, pp. 93-100.

International Search Report and Written Opinion for PCT Application No. PCT/US2022/023466 dated Jul. 5, 2022; 11 pgs.

\* cited by examiner

WEARABLE LIGHT THERAPY DEVICE

CROSS-REFERENCE TO RELATED APPLICATIONS

This application claims priority to U.S. Provisional Patent Application No. 63/171,455, filed Apr. 6, 2021, and U.S. Provisional Patent Application No. 63/214,557, filed Apr. 24, 2021, which are all hereby incorporated in their entirety by reference.

FIELD OF THE INVENTION

The field of the invention is devices and methods for light-based therapy, especially as it relates to red light induced increase in testosterone.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Photobiomodulation, especially with red light, has gained significant attention over the last decades (see e.g., *Semin Cutan Med Surg.* 2013 March; 32(1): 41-52; *Ann Biomed Eng.* 2012 February; 40(2):516-33) and has entered the mainstream in a variety of uses and devices. For example, red and near infrared light treatment has been reported for reduction of wrinkles, skin roughness, etc. (*Photomed Laser Surg.* 2014 Feb. 1; 32(2): 93-100). In further known uses, low level laser therapy combined with intravenous laser blood illumination was implemented for improvement in sexual function (Biomedicine (Taipei). 2018 June; 8(2): 7).

More recently, a variety of consumer devices have also become available for home use to allow individuals to benefit from at least some of the advantages of photobiomodulation. Among other devices, Joovv (URL: joovv.com) offers full body panels for red light therapy, while SolaWave (URL solawave.co) offers small hand-held illuminators with razor format for acne treatment. In still other examples, Bristl (URL: bristlscience.com) a red-light emitting toothbrush is offered to improve dental and periodontal benefits, while Sharper Image offers a hairbrush with red LEDs.

Unfortunately, most consumer devices offer little or no benefits validated by clinical trials. On the other hand, medical uses of photobiomodulation are typically restricted to medical facilities or physician's offices and often require trained professionals and specialized equipment for administration.

Thus, even though various systems and methods of photobiomodulation are known in the art, all or almost all of them suffer from several drawbacks. Therefore, there remains a need for compositions and methods for improved devices and methods of light therapy.

SUMMARY OF THE INVENTION

The inventive subject matter is directed to various devices and methods of wearable photobiomodulation device that can provide illumination of photoresponsive target tissue to so achieve a physiologically desired effect. Most advantageously, illumination can be performed in an inconspicuous manner and does not require dedicated personnel to operate.

In one aspect of the inventive subject matter, the inventor contemplates a wearable photobiomodulation device that includes a shell having an inside surface and an outside surface, and an illumination component that is coupled to the shell and configured deliver light to a portion of a body of an individual wearing the device. It is generally preferred that the inside surface has a shape that contours the portion of the body, and the inside and/or outside surface has an area that (releasably) retains the illumination module. For example, contemplated body portions include the genital area, forearm area, or elbow area.

In typical embodiments the shell includes a retention mechanism that releasably retains the device on the body of the individual, and/or the shell is a molded polymeric shell portion. Preferably, but not necessarily, the illumination component comprises one or more laser diodes or light emitting diodes emitting red light and/or infrared light. For example, the red light and/or infrared light may have a wavelength of about 660 nm or about 880 nm. Where desired, the illumination component further includes a diffuser optically coupled to the one or more laser diodes or the light emitting diodes, and/or a convex lens optically coupled to the one or more laser diodes or the light emitting diodes to allow irradiation at an angle of at least 120 degrees.

In further embodiments, it is contemplated that the illumination component is configured and coupled to the shell such that the light is delivered to the portion of the body over a distance of no more than 5 cm, and/or that the illumination component is configured and coupled to the shell such that light is delivered to a target illumination area of about 100-200 $cm^2$. Most typically, but not necessarily, the illumination component is configured and coupled to the shell such that the light has a dose of between 5-50 $mJ/cm^2$. A rechargeable or disposable power source is typically included as well as a driver circuit that control operation of one or more laser diodes or light emitting diodes.

Consequently, the inventor also contemplates an illumination component that comprises a light emitting device that is electronically coupled to a driver module and a power source, wherein the light emitting device, the driver, and optionally the power source are coupled to a carrier that is configured for attachment and retention on a wearable photobiomodulation device.

For example, the light emitting device may comprise one or more laser diodes or light emitting diodes (e.g., emitting light at a wavelength of about 660 nm or about 880 nm, for example, at a power level of between about 0.1-10 mW). Thus, in at least some embodiments, the light emitting device emits light at a dose of between 5-50 $mJ/cm^2$. Where desired, the light emitting device may comprise a diffuser, and/or may be configured to emit light at over angle of at least 120 degrees. Suitable driver modules will typically control duration, intensity, and/or schedule of illumination for at least one light source in the light emitting device, and/or the optional power source may be a rechargeable or disposable power source.

In further examples, the carrier may be made of or comprise a flexible polymeric material, and optionally include a snap-lock or press fit portion that allows for releasable attachment to the wearable photobiomodulation device. Among other configurations, the light emitting device comprises at least two light emitting diodes or laser diodes that are at least 2-5 cm spaced apart when attached to the wearable photobiomodulation device. Preferably, the light emitting device will comprise a plurality of light sources that illuminate a target illumination area from a distance of no more than 5 cm. In such or other configurations, the light emitting device comprises a plurality of light sources that illuminate a target illumination area of about 100-200 cm$^2$ when attached to the wearable photobiomodulation device. when attached to the wearable photobiomodulation device.

Therefore, the inventor also contemplates a wearable device that comprises a shell having an inside surface and an outside surface, wherein the inside surface has a shape that contours a portion of a body of an individual wearing the device, and wherein the inside surface and/or outside surface has an area that is configured to retain an illumination module.

Most typically at least some or even all of the shell is made from a polymeric material, and the body portion that is contoured is a genital area, a forearm area, or an elbow area. For example, the shell may be configured as a sports cup. In further contemplated embodiments, the area that is configured to retain the illumination component may comprise an indentation or cutout that corresponds to the shape of the illumination component.

In yet further aspects of the inventive subject matter, the inventor contemplates a method of effecting photobiomodulation in an individual that has a step of providing a wearable photobiomodulation device as presented herein, and a further step of attaching or causing to attach the wearable photobiomodulation device to the individual such that the wearable photobiomodulation device delivers a dose of light to a photoresponsive tissue of the individual. Finally, the dose of light is delivered to the individual using the wearable photobiomodulation device.

For example, the wearable photobiomodulation device may be attached to the individual (e.g., to the genital area, a forearm area, or an elbow area of the individual) for a time between 10 and 60 minutes while delivering the dose of light. It is further contemplated that the dose is delivered to a target illumination area of about 100-200 cm$^2$, and that the light is red light and/or infrared light (e.g., having a wavelength maximum of about 660 nm or 880 nm). While not limiting to the inventive subject matter, it is typically preferred that the dose of light is between 5-50 mJ/cm$^2$, and/or that the dose of light is administered no more than 3 hours prior to bedtime of the individual. Most typically, but not necessarily, the dose of light is administered in a continuous fashion. Advantageously, the dose of light in such method will increase the blood level of a reproductive hormone in the individual, improve fertility in the individual, and/or increase muscle mass in the individual.

Therefore, and viewed form a different perspective, the inventor also contemplates a method of increasing a blood level of a reproductive hormone in an individual that includes a step of providing a wearable photobiomodulation device as presented herein and a further step of attaching or causing to attach the wearable photobiomodulation device to the individual such that the wearable photobiomodulation device delivers a dose of light to a photoresponsive tissue of the individual, wherein the dose of light increases the blood level of the reproductive hormone in the individual.

For example, the photoresponsive tissue is scrotal tissue, the light is red light and/or infrared light, and/or the dose of light is between 5-50 mJ/cm$^2$. Most typically, the dose of light is delivered in a continuous fashion, and/or is administered no more than 3 hours prior to bedtime of the individual. Among other entities, contemplated reproductive hormones include testosterone, estrogen, follicle stimulating hormone (FSH), luteinizing hormone (LH), or dihydroxy epiandrosterone (DHEA). As will be readily appreciated, contemplated methods may be employed with healthy individuals (and especially individuals above the age of 40), but also to those diagnosed with hypogonadism. In at least some embodiments, the blood level of the reproductive hormone will increase by at least 10%.

Viewed from still another perspective, the inventor also contemplates a method of improving fertility in an individual that includes a step of providing a wearable photobiomodulation device as presented herein, and a step of attaching or causing to attach the wearable photobiomodulation device to the individual such that the wearable photobiomodulation device delivers a dose of light to a photoresponsive tissue of the individual, wherein the dose of light increases fertility of the individual. Preferably, the dose of light will modulate estrogen, FSH, and/or LH to thereby increase the fertility.

Viewed from a still further perspective, the inventor contemplates a method of increasing muscle mass in an individual that includes a step of providing a wearable photobiomodulation device as presented herein, and another step of attaching or causing to attach the wearable photobiomodulation device to the individual such that the wearable photobiomodulation device delivers a dose of light to a photoresponsive tissue of the individual, wherein the dose of light increases muscle mass of the individual. While not limiting to any theory or hypothesis, the inventor contemplates that the dose of light increases testosterone to thereby increase the muscle mass.

Consequently, a wearable photobiomodulation device as presented herein is deemed suitable for use in medicine. Such medicinal uses may lead to improvement of one or more physical, physiological, and emotional characteristics and performance indicators of the user. Among other suitable uses, especially preferred uses include use to increase muscle mass in an individual, improve fertility in an individual, and/or increase the blood level of a reproductive hormone in an individual.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
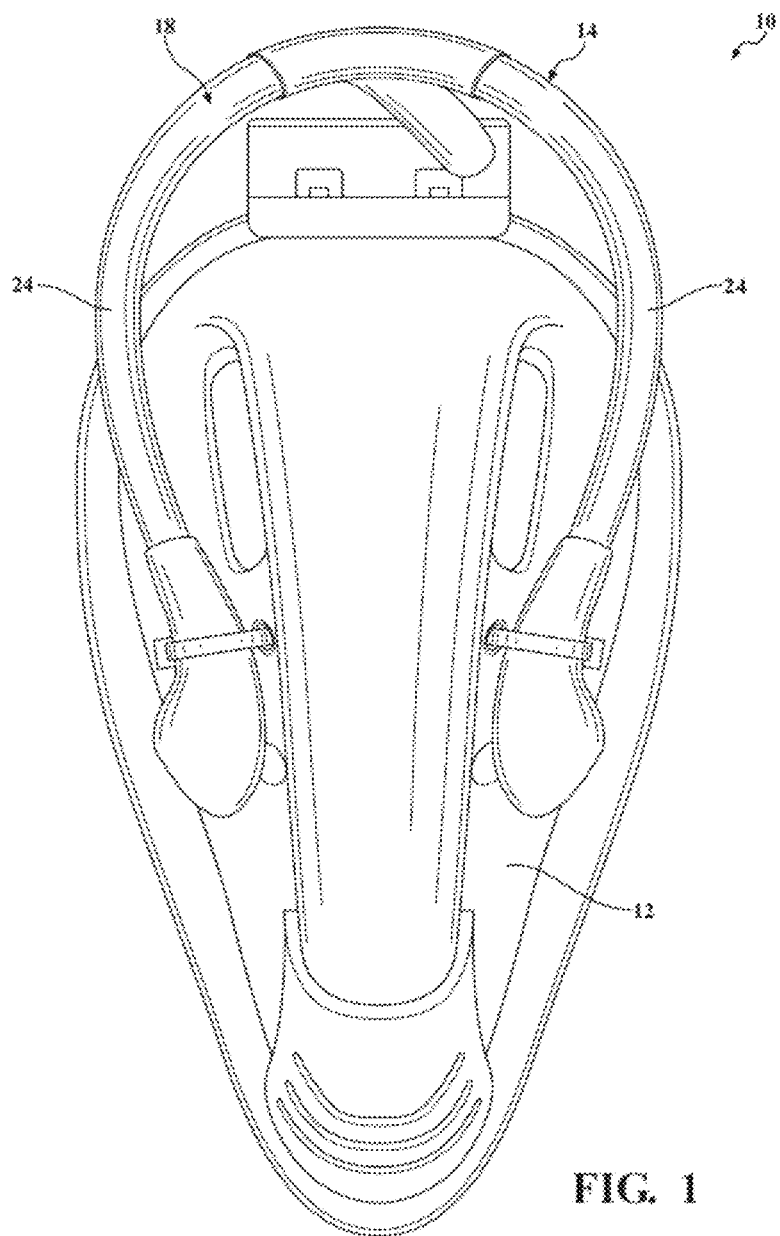
FIG. 1 is a top view of an exemplary photobiomodulation device as presented herein.
Figure 2:
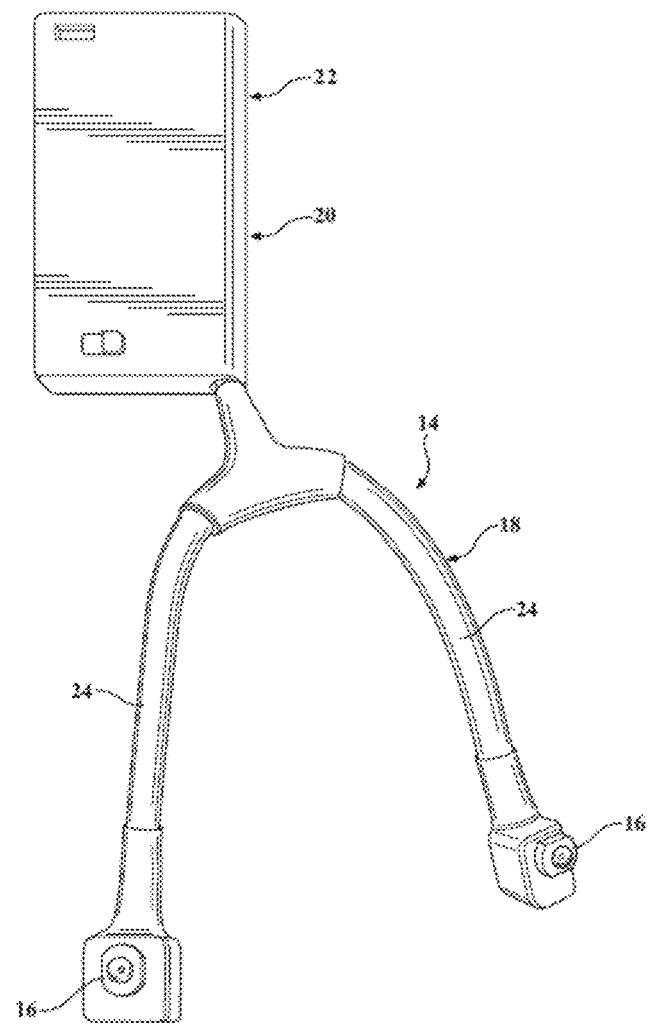
FIG. 2 is a top view of an exemplary illumination module as presented herein.
Figure 3:
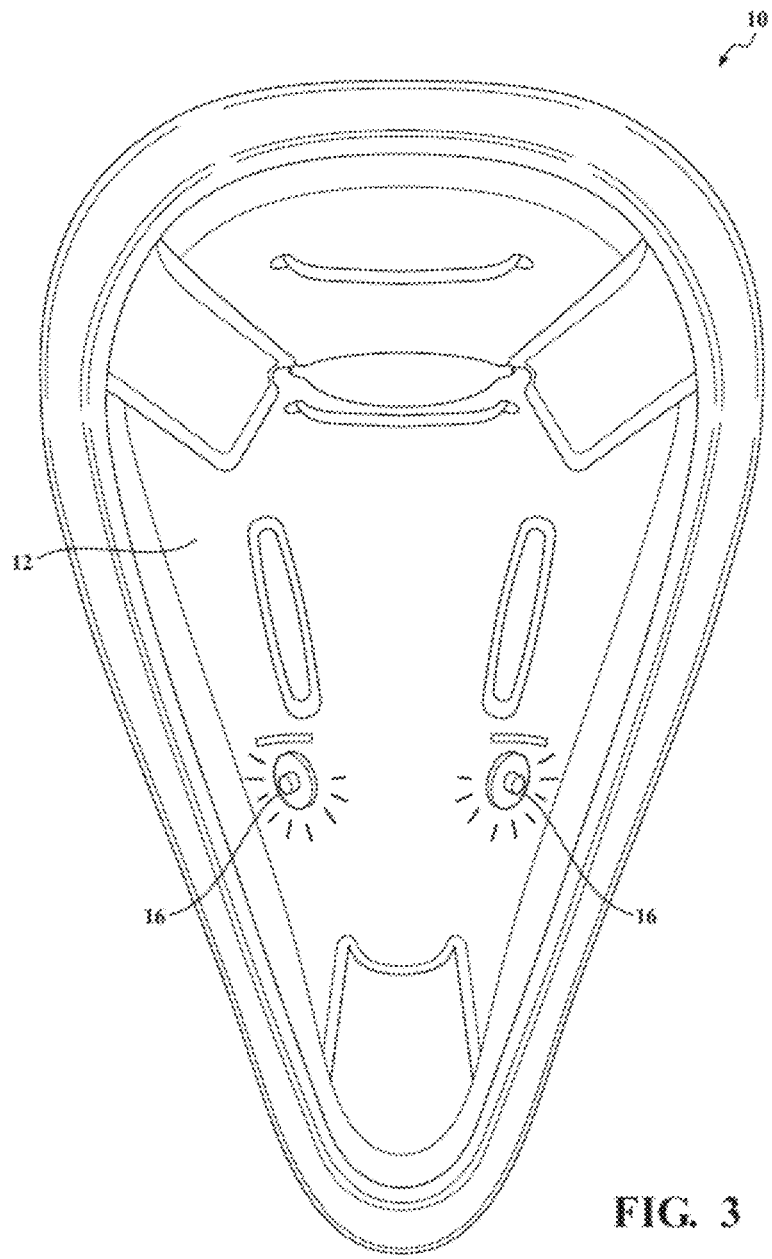
FIG. 3 is an inside view of an exemplary photobiomodulation device with active illumination module as presented herein.
Figure 4:
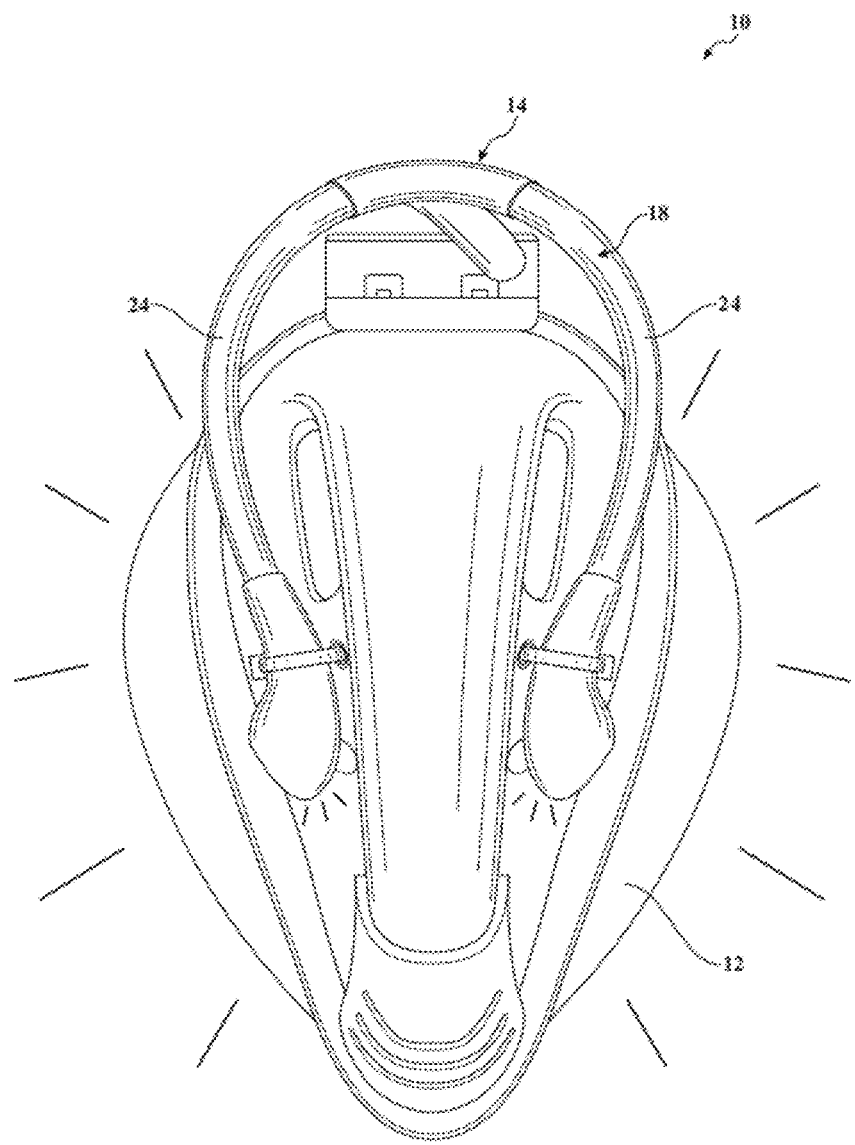
FIG. 4 is a top view of the photobiomodulation device of FIG. 3.
Figure 5:
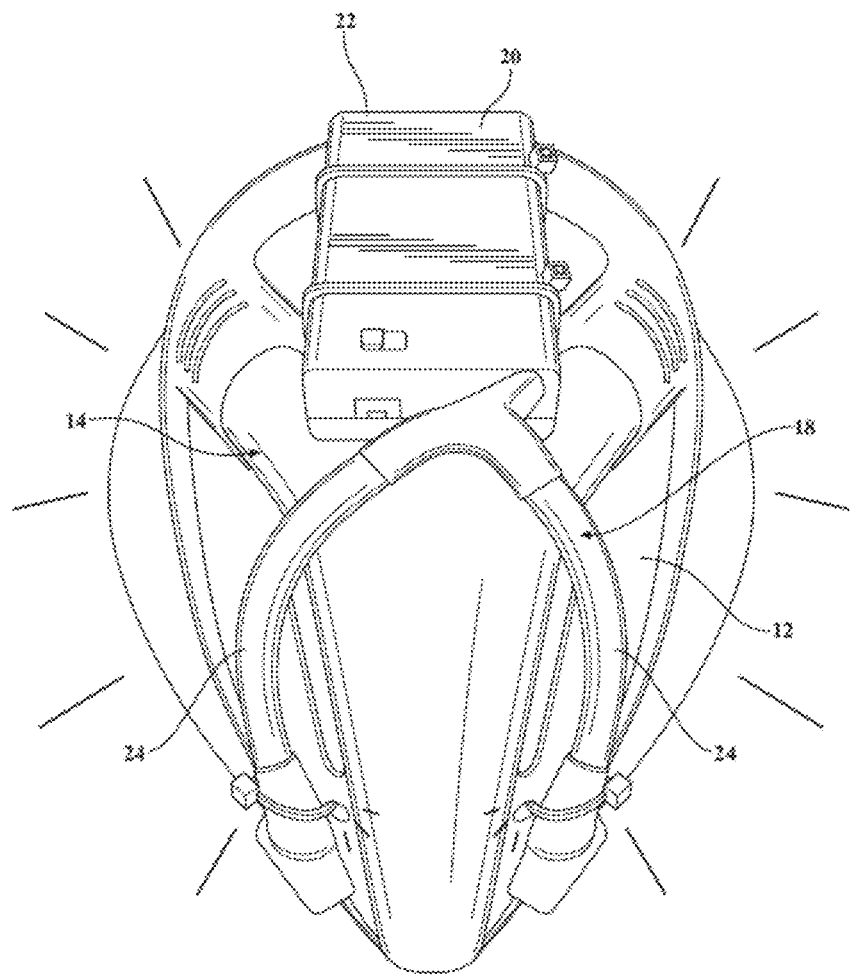
FIG. 5 is another top view of the photobiomodulation device of FIG. 3.
Figure 6:
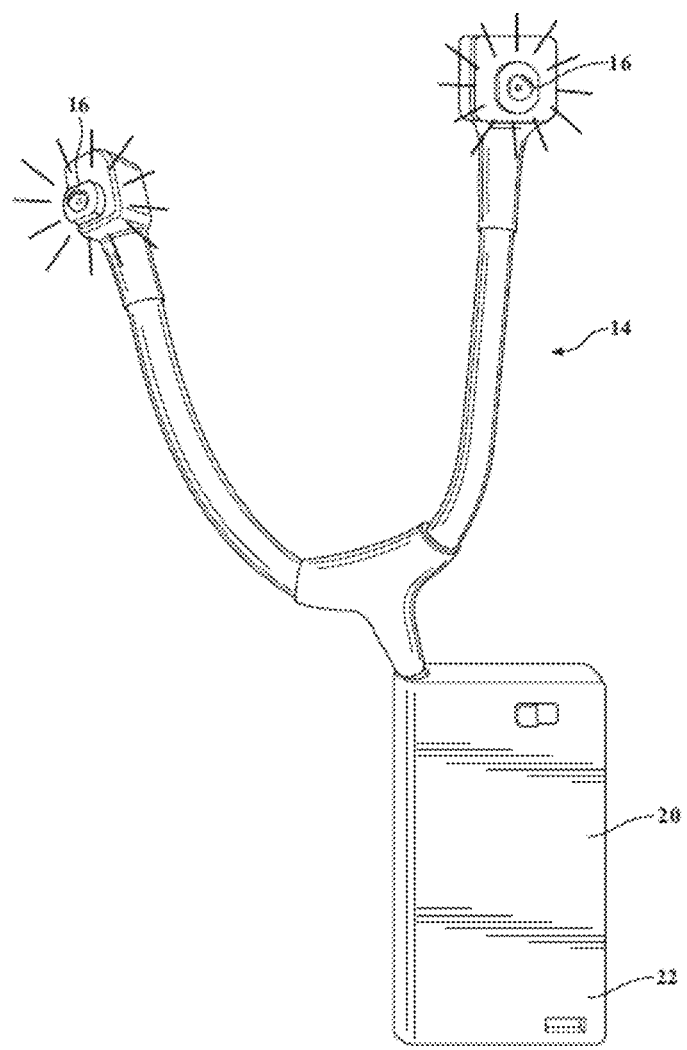
FIG. 6 is a top view of the active illumination module of FIG. 2.

The inventor has now discovered that photobiomodulation can be performed in a simple and effective manner that provides a desired effect while allowing an individual to apply the treatment in the privacy and comfort of a home setting. Most preferably, and with reference to FIGS. 1-6, illumination is provided from a wearable device 10 that has a shell 12 and an illumination component 14. As will be readily appreciated, where the shell 12 is configured to conform or contour a portion of the body (such as the genital area, a forearm area, knee area, ankle area, shoulder area, or an elbow area), the wearable device 10 can be attached to the body and worn in an inconspicuous manner.

Moreover, as the shell 12 contours the portion of the body that comprises photoresponsive tissue, illumination can be directed at the photoresponsive tissue in a manner that allows coverage of a larger area (e.g., using a diffuser and/or convex lens) without the need for multiple light guides or large number of light sources 16. Most advantageously, the illumination component 14 will comprise multiple LEDs and/or laser diodes that emit light at a desired wavelength and power to achieve a therapeutically effective dose of light. However, as described in greater detail below, it is to be appreciated that light guides, lenses, reflective materials, or other materials may used to augment the light generated by the illumination component.

In one example, the shell 12 is configured as a sports cup that can be worn as such, however, will also include a detachable illumination component 14 that comprises two light sources 16 (e.g., LEDs) with a spectral maximum of about 660 nm and a spectral width of +/−20 nm relative to the maximum. Each LED has a power of 5 mW and is coupled to a carrier 18 and electronically coupled to a driver module 20 and rechargeable power source 22. The carrier 18 and LEDs are releasably coupled to the outer surface of the shell such that the LEDs point towards the inside of the cup. The driver module 20 is programmed to deliver continuous illumination via the LEDs to the photoresponsive tissue (here: scrotal and underlying testicular tissues), for example, at a dose of about 20 mJ/cm$^2$ for a duration of about 30 min. In various embodiments, the dose may from about 1 mJ/cm$^2$ to about 200 mJ/cm$^2$, from about 1 mJ/cm$^2$ to about 100 mJ/cm$^2$, from about 1 mJ/cm$^2$ to about 50 mJ/cm$^2$, from about 10 mJ/cm$^2$ to about 30 mJ/cm$^2$, or from about 15 mJ/cm$^2$ to about 25 mJ/cm$^2$. Both LEDs are optically coupled to a convex lens and diffuser that allows for illumination over an angle of at least 120 degrees. In such arrangement, it should be appreciated that the LED need not directly contact the photoresponsive tissue, but the surface of the LED can be positioned up to 5 cm away from the photoresponsive tissue. Consequently, it should be appreciated that the target illumination area may be as large as about 100-200 cm$^2$. FIGS. 1-6 depict exemplary devices contemplated herein.

While illumination can be performed at any time of day, it is noted that illumination is preferably performed in the evening, such as less than about 3 hours from bedtime to stimulate testosterone production during the parasympathetic phase of the overnight rest period. As such, it should be recognized that testosterone levels can be boosted (as compared to average measurements under otherwise same conditions but without illumination) by at least 10% when measured in saliva in the morning within 1 hour of rising. However, in further embodiments, it is contemplated that the illumination can also be performed upon awakening and/or before rising. Therefore, illumination in the morning (e.g., more than 2 hours before noon, or more than 3 hours before noon, or more than 4 hours before noon, or more than 5 hours before noon) is also expressly contemplated herein. In various embodiments, due to circadian variations of testosterone levels in users of the wearable device 10, administration may occur in the morning, in the afternoon, the evening, after waking up, before attempting to sleep, or combinations thereof.

With respect to the shell 12, it should be appreciated that the shell shape need not be limited to a sports cup, but that the shell can have any configuration that conforms with or contours to a portion of a body of an individual (or non-human mammal). Most typically, the portion of the body will contain at least some photoresponsive tissue. As used herein, the term "photoresponsive tissue" refers to a tissue that upon irradiation with light, and especially red light and/or infrared light gives directly or indirectly rise to a physiological response such as hormone release or production that is systemically measurable. While not limiting to the inventive subject matter, it is contemplated that especially photoreceptive tissues are those tissues that are ordinarily covered by clothing or otherwise protected from or inaccessible to daylight (e.g., genital tissue, buccal tissue, underarm/armpit tissue, tissue at the sole of a foot, etc.) and as such may be significantly more photoreceptive and/or photoresponsive. In preferred aspects, the photoresponsive tissue is directly irradiated (i.e., without a layer of clothing between the tissue and the light source), but in other aspects, a layer of clothing or other material may also be placed between the tissue and the light source, so long as the clothing or other material will not absorb the emitted light in a substantial manner (e.g., absorbs more than 50%, or more than 60%, or more than 70%, or more than 80% of the emitted light). Consequently, the shell may be configured as a sports cup, as a shell that at partially encloses a section of an arm or leg, a shell that conforms to or contours at least a portion of the skull, etc. In various embodiment, the shell 12 includes a polymeric material (e.g., similar to a sport cup), fibrous material (e.g., a cotton underwear), a film (e.g., a form-fitting film that at least partially encapsulates the scrotum), or combination thereof.

Most typically, the shell 12 will be manufactured from a polymeric material such as HDPE, PE, PET, and/or PP, and will be at least somewhat flexible upon application of manual force. Moreover, it is contemplated that the shell will include one or more attachment implements such as elastic straps or belts so that the shell can be retained on the body of an individual. In still further contemplated aspects, it is preferred that the shell 12 will include one or more portions that allow for attachment or coupling of one or more illumination components 14. Most typically, the portion(s) will allow for releasable attachment and may therefore contain a snap or other press-fit implement. In addition, the portion(s) will be recessed or otherwise open to accommodate at least a part of the illumination component 14. For example, suitable attachment portions include channels and eve openings that are configured to receive at least a portion of the illumination component 14.

While not limiting to the inventive subject matter, the illumination component 14 may be fabricated or disposed on the carrier 18 to which are coupled one or more light sources 16 (such as an LED or laser diode), a driver module, and optionally a power source. Thus, in at least some aspects of the inventive subject matter, the illumination component 14 may be attached to and/or removed from the shell 12 in a single piece and re-attached to the same type or different type of a shell 12. Among other benefits of such configurations, sanitation and interchangeability of the device components will be significantly simplified. In some embodiments, the carrier 18 may have at least two distinct and preferably flexible arms to which the light source(s) are coupled (see FIGS. 1-6). Advantageously, such flexible arms may be used to better conform the carrier 18 to the shell 12. For example, the arms 24 may extend form the rest of the carrier 18 at an angle to so form a Y-shape with the rest of the carrier 18.

Figure 7:
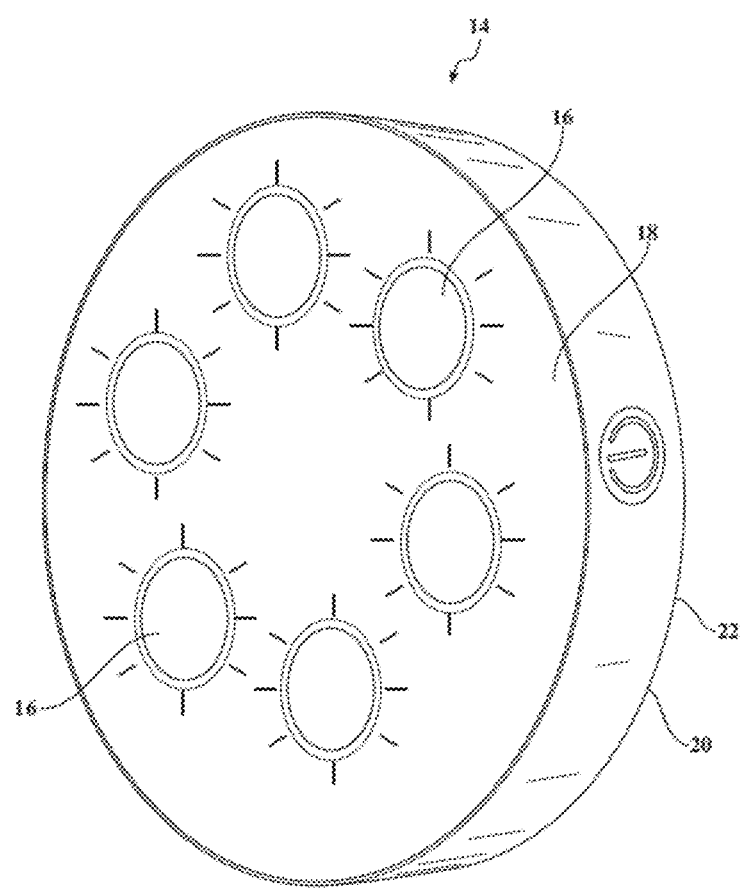
FIG. 7 is a top view of another active illumination module as presented herein.
Figure 8:
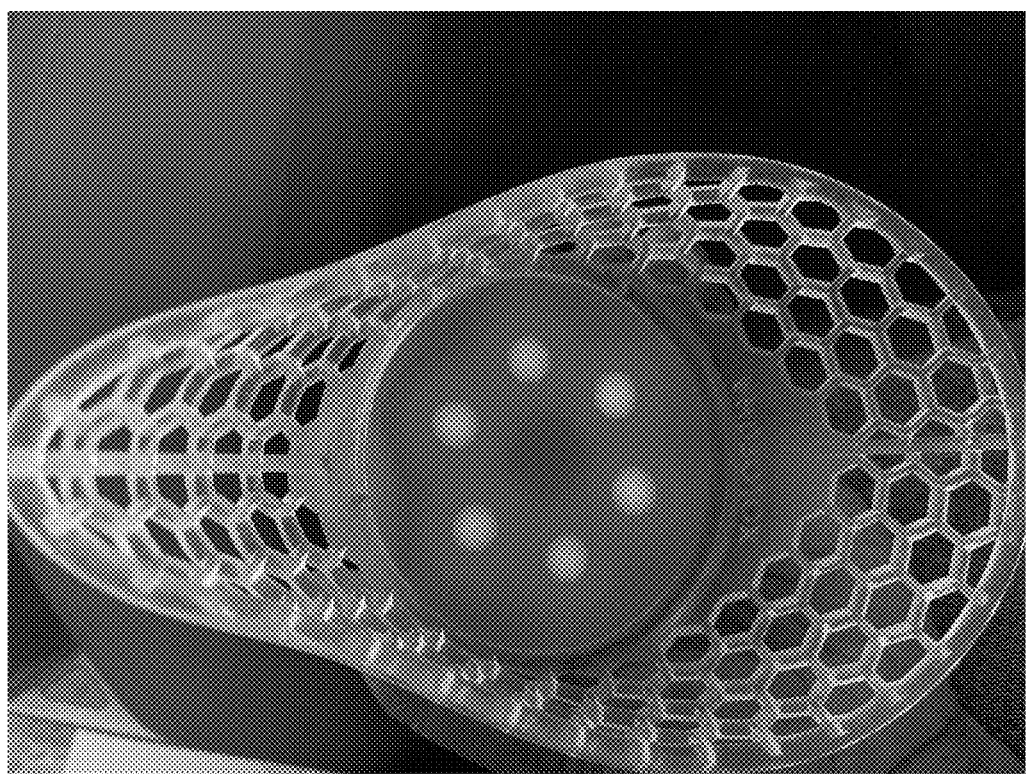
FIG. 8 is an inside view of another exemplary photobiomodulation device with the illumination module of FIG. 7.

In other embodiments, the illumination component 14 is in the form of a puck which includes the one or more light sources 16 (see FIG. 7). Of course, it should also be appreciated that the type and number of light sources in an illumination component 14 may vary considerably, and suitable wearable devices 10 may include between 1-4 light sources 16, or between 2-6 light sources 16, or between 5-10 light sources 16, and even more. Moreover, it should be recognized that the type of light source 16 may vary, and all known types of light sources 16 are deemed suitable for use herein. However, especially preferred light sources 16 include OLEDs, LEDs, laser diodes, and various other solid-state emitters. Most typically, the light source 16 will be monochromatic (i.e., within a spectral range of 60 nm). However, in at least some embodiments, the light source 16 may be polychromatic, and especially contemplated polychromatic light sources 16 include multicolor LEDs that can be controlled to emit a variety of light colors. FIG. 8 exemplarily depicts another exemplary photobiomodulation device using the illumination component of FIG. 7, where the shell is configured as a webbed shell to so include a plurality of openings that facilitate equilibration of temperature and air between a space inside the device when worn by a user and the outside.

Most preferred light sources 16 will emit light in the red and infrared area of the spectrum. Therefore, suitable wavelengths will be at least 580 nm, or at least 600 nm, or at least 620 nm, or at least 640 nm, or at least 660 nm, or at least 680 nm, or at least 700 nm, or at least 720 nm, or at least 740 nm, or at least 760 nm, or at least 780 nm, or at least 800 nm, or at least 820 nm, or at least 840 nm, or at least 860 nm, or at least 880 nm, and even longer. Moreover, and as already noted above, the wearable photobiomodulation device may include multiple and distinct light sources 16 that emit, for example light at a maximum of about 660 nm and at a maximum of about 880 nm.

Most typically, the power level of suitable light sources 16 will be at least 0.01 mW, or at least 0.1 mW, or at least 0.5 mW, or at least 1 mW, or at least 2 mW, or at least 5 mW, or at least 10 mW, or at least 50 mW, or at least 100 mW, or at least 250 mW, or at least 500 mW, or at least 750 mW, and even higher. For example, suitable light sources will have a power output of at least 0.1-1.0 mW, or 1-5 mW, or 5-50 mW, 50-500 mW, and higher. Therefore, the dose that can be delivered from contemplated devices can be at least 1.0 mJ/cm$^2$, or at least 5.0 mJ/cm$^2$, or at least 10 mJ/cm$^2$, or at least 20 mJ/cm$^2$, or at least 30 mJ/cm$^2$, or at least 50 mJ/cm$^2$, and even higher.

As noted earlier, it should also be appreciated that the light sources 16 will have a diffuser and/or other optical element such as a convex lens to allow dispersion of the emitted light over at least 90 degrees, or at least 120 degrees, or at least 150 degrees, or at least 180 degrees. As should be appreciated, such light dispersion will be particularly beneficial where the light source 16 does not directly contact the photoresponsive tissue. Alternatively, or additionally, it is contemplated that where the light source 16 is not a point source, wide area illumination can also be achieved with rectangular or otherwise linearly extended light sources (e.g., LED band or rectangular LED). Moreover, it is also contemplated that light guides and light transmitting fabrics or cloth can be used to illuminate larger areas. For example, the wearable device 10 may be configured such that the distance between the light source 16 is between about 0.1-1.0 cm, or between about 1.0-2.0 cm, or between about 1.0-3.0 cm, or between about 2.0-4.0 cm, or between about 1.0-5.0 cm. Thus, suitable distances especially include those less than 5 cm, or less than 4 cm, or less than 3 cm, or less than 2 cm, or less than 1 cm, but preferably more than 0.1 cm. Consequently, it should be appreciated that the light that is being delivered will be substantially uniform at the target tissue and may even cover areas that would otherwise be obscured by wrinkles or skin folds. Viewed form a different perspective, the target illumination area that can be achieved using the devices contemplated herein can be at least 10 cm$^2$, or at least 25 cm$^2$, or at least 50 cm$^2$, or at least 100 cm$^2$, or at least 150 cm$^2$, or at least 200 cm$^2$, or at least 250 cm$^2$, and even larger.

As will be readily appreciated, the operation of the light sources 16 can be controlled from the driver module 20 that may be programmed to operate in a distinct fashion, and/or that may electronically communicate with a second control device (e.g., mobile phone running an app via Bluetooth). Power is typically delivered from a rechargeable or disposable battery 22, which may or not be part of the illumination component 14.

In various embodiments, a system for effecting photobiomodulation in an individual is provided. The system includes the wearable device 10, the second controller, and one or more biofeedback devices. As readily appreciated, the driver module 20 of the wearable device 10 may communicate with second controller (e.g., a mobile phone). The second controller may electronically communicate with the biofeedback devices (e.g., smartwatch, heartrate monitor, wearable hormone sensor, and the like) to augment illumination of the target tissue using the wearable device 10.

In most embodiments, illumination will be continuous at the same power level using the same light wavelengths. However, it should also be recognized that alternative modes may provide further benefits. For example, illumination may be discontinuous (regular intermittent or random intermittent) to reduce tissue heating and/or accommodation to the stimulus. Likewise, the wavelength may be switched (e.g., from red to infrared) to maximize or 'stack' biological effects achieved by each wavelength. Similarly, intensity may be varied (e.g., in a sine wave pattern) at a desired frequency to 'tune into' specific physiological resonance. Of course, where multiple wavelengths are being used, change from one to the other wavelength may be gradual or abrupt. In most cases, illumination will be limited to a specific time and/or cumulative energy dose and the person of ordinary skill in the art will be readily apprised on how to program a drive module to that effect.

In some embodiments, the wearable device 10 may include one or more additional components for modulating temperature of the target tissue (e.g., ventilation or heating elements), modulating moisture level proximate the target tissue (e.g., water vapor sources, desiccants, or ventilation), and modulating exposure of the illumination to the target tissue (e.g., optical filters or partially or fully opaque films).

In addition, it should be appreciated that the illumination schedule can also be used to enhance or extend a circadian or monthly rhythm, and especially such rhythm with regard to reproductive hormones. For example, where DHEA or testosterone is to be increased, illumination may be performed in the evening, at night, near bedtime, etc., or even in the morning. On the other hand, where estrogen, LH, or FSH is to be increased, illumination can be performed at the appropriate times over the menstruation cycle. Moreover, it should be noted that pharmaceutical and/or nutraceutical intervention may be used to enhance the effect of the illumination. For example, where testosterone is to be enhanced, various herbal and vitamin formulations can be concurrently administered. Testosterone is then tested in whole blood or saliva following protocols well known in the art.

Based on the increase in reproductive hormones, it is contemplated that illumination using the devices and methods presented herein may increase hormone levels per se (e.g., FSH, LH, estrogen, DHEA, testosterone), as well as hormone associated subjective and objective markers such as physical/psychometric markers including ED, confidence, muscle mass increase, energy, semen quality, ejaculation speed, fat loss, fertility, appetite, carb/meat craving, hair growth/density, sleep, anxiety, mood, dreams, back pain, etc.

Typical administration schedules therefore include daily, or twice weekly, thrice weekly, four time weekly sessions lasting at least 10 minutes, or at least 20 minutes, or at least 30 minutes, or at least 45 minutes over a span of at least 1 week, more typically at least 2 weeks, or at least 3 weeks, or at least 4 weeks. Hormone (and especially testosterone) level increases can therefore be at least 2%, or at least 5%, or at least 7.5%, or at least 10%, or at least 12%, or at least 15%, or at least 17%, or at least 20%, and even higher (as compared to the same test regime without illumination).

EXAMPLES

In a set of experiments, subjects were treated with light generated by exemplary wearable devices. In particular, the groin areas of male subjects were exposed to light having a wavelength of 660 nanometers to evaluate the impact of the light on physical, physiological, and emotional characteristics and performance indicators of the subjects. The results of the evaluation are found in Examples 1 to 19 below.

Example 1: Evaluation of Satisfaction Level of Subjects

The profiles of the subjects and the frequency of the exposure to the light by the subjects ("Exposure Period") are provided in Table 1 below. After completion of the Exposure Period, the subjects were asked to provide their overall satisfaction level to the light treatment on a scale from 1 to 10 with 10 being the highest satisfaction level. The results were recorded as provided in Table I below.

TABLE I

Results of the Evaluation of Example 1

| Subject | 1 | 2 | 3 | 4 | 5 | 6 | 7 | 8 | 9 | 10 | Avg. |
|---|---|---|---|---|---|---|---|---|---|---|---|
| Age | 28 | 34 | 40 | 38 | 39 | 30 | 25 | 55 | 53 | 59 | 40.1 |
| BMI | 26 | 32 | 26 | 35 | 27 | 25 | 28 | 34 | 34 | 23 | 29 |
| Time of day for Exposure (24-hour Clock) | 6 | 8 | 7 | 10 | 18 | 12 | 8 | 23 | 7 | 7 | 10.6 |
| Frequency of Exposure per Week (Days) | 3 | 5 | 4 | 3 | 3 | 5 | 4 | 5 | 4 | 3 | 3.9 |
| Total Number of Exposures | 24 | 20 | 32 | 24 | 36 | 20 | 30 | 20 | 24 | 24 | 25.4 |
| Duration of each Exposure (Minutes) | 30 | 30 | 30 | 30 | 30 | 30 | 30 | 30 | 30 | 30 | 30 |
| Overall Satisfaction after Exposure Period (Scale) | 10 | 10 | 10 | 9 | 10 | 9 | 10 | 10 | 8 | 8 | 9.4 |

As shown in Table I above, the exemplary wearable device received an average rating of 9.4 points out of 10 points for satisfaction over all the subjects. In particular, the subjects were overwhelmingly satisfied with the use of the exemplary wearable device as at least related to the frequency and duration of use. Further, the subjects were overwhelmingly satisfied with the efficacy of the exemplary wearable device as at least related to the improvement in physical, physiological, and emotional characteristics and performance indicators described in Examples 2 to 19 below.

Example 2: Evaluation of Energy Level of Subjects

Prior to exposure to the light, the subjects were asked to provide their energy level on a scale from 1 to 10 with 10 being the highest energy level. After completion of the Exposure Period as described in Example 1, the subjects were asked once again to provide their energy level on the scale from 1 to 10. The results were recorded as provided in Table II below.

TABLE II

Results of the Evaluation of Example 2

| Subject | 1 | 2 | 3 | 4 | 5 | 6 | 7 | 8 | 9 | 10 | Avg. |
|---|---|---|---|---|---|---|---|---|---|---|---|
| Energy Level prior to Exposure Period (Scale) | 7 | 7 | 3 | 5 | 4 | 7 | 7 | 5 | 5 | 5 | 5.5 |
| Energy Level after Exposure Period (Scale) | 9 | 8 | 9 | 6 | 7 | 9 | 10 | 7 | 7 | 7 | 7.9 |
| Improvement (Scale) | 2 | 1 | 6 | 1 | 3 | 2 | 3 | 2 | 2 | 2 | 2.4 |
| Improvement (Percent) | 29% | 14% | 200% | 20% | 75% | 29% | 43% | 40% | 40% | 40% | 44% |

As shown in Table II above, exposure to the light generated by the exemplary wearable device resulted in an average increase in energy level over all the subjects by 2.4 points or 44%.

Example 3: Evaluation of Sleep Duration of Subjects

Prior to exposure to the light, the subjects were asked to sleep for a first sleep period and provide the sleep duration in hours of the first sleep period. After completion of the Exposure Period as described in Example 1, the subjects were asked once again sleep for a second sleep period and provide the sleep duration in hours of the second sleep period. The results were recorded as provided in Table III below.

TABLE III

Results of the Evaluation of Example 3

| Subject | 1 | 2 | 3 | 4 | 5 | 6 | 7 | 8 | 9 | 10 | Avg. |
|---|---|---|---|---|---|---|---|---|---|---|---|
| Sleep Duration prior to Exposure Period (Hours) | 7 | 6 | 8 | 7 | 5 | 7 | 7 | 7 | 7 | 8 | 6.9 |
| Sleep Duration after Exposure Period (Hours) | 8 | 7 | 8 | 7 | 7 | 7 | 9 | 7 | 7 | 7 | 7.4 |
| Improvement (Horns) | 1 | 1 | 0 | 0 | 2 | 0 | 2 | 0 | 0 | −1 | 0.5 |
| Improvement (Percent) | 14% | 17% | 0% | 0% | 40% | 0% | 29% | 0% | 0% | −13% | 7% |

As shown in Table III above, exposure to the light generated by the exemplary wearable device resulted in an average increase in sleep duration over all the subjects by 30 minutes or 7%.

Example 4: Evaluation of Sleep Onset of Subjects

Prior to exposure to the light, the subjects were asked to attempt to sleep for a first sleep period and provide the number of minutes needed to sleep ("Sleep Onset") for the first sleep period. After completion of the Exposure Period as described in Example 1, the subjects were asked once again to attempt to sleep for a second sleep period and provide the Sleep Onset for the second sleep period. The results were recorded as provided in Table IV below.

TABLE IV

Results of the Evaluation of Example 4

| Subject | 1 | 2 | 3 | 4 | 5 | 6 | 7 | 8 | 9 | 10 | Avg. |
|---|---|---|---|---|---|---|---|---|---|---|---|
| Sleep Onset prior to Exposure Period (Minutes) | 20 | 5 | 30 | 15 | 20 | 15 | 40 | 15 | 25 | 20 | 20.5 |
| Sleep Onset after Exposure Period (Minutes) | 10 | 5 | 30 | 15 | 30 | 5 | 15 | 30 | 20 | 30 | 19 |
| Improvement (Minutes) | −10 | 0 | 0 | 0 | 10 | −10 | −25 | 15 | −5 | 10 | −1.5 |
| Improvement (Percent) | −50% | 0% | 0% | 0% | 50% | −67% | −63% | 100% | −20% | 50% | −7% |

As shown in Table IV above, exposure to the light generated by the exemplary wearable device resulted in an average decrease in sleep onset over all the subjects by 1.5 minutes or 7%.

Example 5: Evaluation of Libido Level of Subjects

Prior to exposure to the light, the subjects were asked to provide their libido level on a scale from 1 to 10 with 10 being the highest libido level. After completion of the Exposure Period as described in Example 1, the subjects were asked once again to provide their libido level on the scale from 1 to 10. The results were recorded as provided in Table V below.

TABLE V

Results of the Evaluation of Example 5

| Subject | 1 | 2 | 3 | 4 | 5 | 6 | 7 | 8 | 9 | 10 | Avg. |
|---|---|---|---|---|---|---|---|---|---|---|---|
| Libido Level prior to Exposure Period (Scale) | 9 | 8 | 3 | 3 | 2 | 8 | 6 | 5 | 2 | 5 | 5.1 |
| Libido Level after Exposure Period (Scale) | 9 | 9 | 7 | 5 | 8 | 8 | 9 | 5 | 5 | 5 | 7 |
| Improvement (Scale) | 0 | 1 | 4 | 2 | 6 | 0 | 3 | 0 | 3 | 0 | 1.9 |
| Improvement (Percent) | 0% | 13% | 133% | 67% | 300% | 0% | 50% | 0% | 150% | 0% | 37% |

As shown in Table V above, exposure to the light generated by the exemplary wearable device resulted in an average increase in libido level over all the subjects by 1.9 points or 37%.

Example 6: Evaluation of Sex Duration of Subjects

Prior to exposure to the light, the subjects were asked to perform sexual intercourse for a first intercourse period and provide the number of minutes that intercourse was maintained ("Sex Duration") for the first intercourse period. After completion of the Exposure Period as described in Example 1, the subjects were asked to perform sexual intercourse for a second intercourse period and provide the Sexual Duration for the second intercourse period. The results were recorded as provided in Table VI below.

TABLE VI

Results of the Evaluation of Example 6

| Subject | 1 | 2 | 3 | 4 | 5 | 6 | 7 | 8 | 9 | 10 | Avg. |
|---|---|---|---|---|---|---|---|---|---|---|---|
| Sex Duration prior to Exposure Period (Minutes) | 15 | 20 | 10 | 5 | 5 | 20 | 10 | 10 | 5 | 10 | 11 |
| Sex Duration after Exposure Period (Minutes) | 30 | 30 | 25 | 7 | 20 | 25 | 10 | 10 | 10 | 10 | 17.7 |
| Improvement (Minutes) | 15 | 10 | 15 | 2 | 15 | 5 | 0 | 0 | 5 | 0 | 6.7 |
| Improvement (Percent) | 100% | 50% | 150% | 40% | 300% | 25% | 0% | 0% | 100% | 0% | 61% |

As shown in Table VI above, exposure to the light generated by the exemplary wearable device resulted in an average increase in sexual duration over all the subjects by 6.7 minutes or 61%.

Example 7: Evaluation of Hardness Level of Subjects

Prior to exposure to the light, the subjects were asked to provide the hardness level of their penis on a scale from 1 to 10 with 10 being the highest hardness level. After completion of the Exposure Period as described in Example 1, the subjects were asked once again to provide their hardness level on the scale from 1 to 10. The results were recorded as provided in Table VII below.

TABLE VII

Results of the Evaluation of Example 7

| Subject | 1 | 2 | 3 | 4 | 5 | 6 | 7 | 8 | 9 | 10 | Avg. |
|---|---|---|---|---|---|---|---|---|---|---|---|
| Hardness Level prior to Exposure Period (Scale) | 9 | 7 | 6 | 6 | 2 | 8 | 7 | 7 | 5 | 7 | 6.4 |
| Hardness Level after Exposure Period (Scale) | 9 | 9 | 7 | 7 | 9 | 8 | 10 | 8 | 6 | 7 | 8 |
| Improvement (Scale) | 0 | 2 | 1 | 1 | 7 | 0 | 3 | 1 | 1 | 0 | 1.6 |
| Improvement (Percent) | 0% | 29% | 17% | 17% | 350% | 0% | 43% | 14% | 20% | 0% | 25% |

As shown in Table VII above, exposure to the light generated by the exemplary wearable device resulted in an average increase in hardness level over all the subjects by 1.6 points or 25%.

Example 8: Evaluation of Orgasm Duration of Subjects

Prior to exposure to the light, the subjects were asked to perform sexual intercourse for a first intercourse period and provide the number of seconds that their orgasm was maintained ("Orgasm Duration") for the first intercourse period. After completion of the Exposure Period as described in Example 1, the subjects were asked to perform sexual intercourse for a second intercourse period and provide the Orgasm Duration for the second intercourse period. The results were recorded as provided in Table VIII below.

TABLE VIII

Results of the Evaluation of Example 8

| Subject | 1 | 2 | 3 | 4 | 5 | 6 | 7 | 8 | 9 | 10 | Avg. |
|---|---|---|---|---|---|---|---|---|---|---|---|
| Orgasm Duration prior to Exposure Period (Seconds) | 5 | 3 | 3 | 3 | 5 | 5 | 20 | 4 | 5 | 3 | 5.6 |
| Orgasm Duration after Exposure Period (Seconds) | 5 | 4 | 3 | 3 | 8 | 5 | 30 | 4 | 10 | 3 | 7.5 |
| Improvement (Seconds) | 0 | 1 | 0 | 0 | 3 | 0 | 10 | 0 | 5 | 0 | 1.9 |
| Improvement (Percent) | 0% | 33% | 0% | 0% | 60% | 0% | 50% | 0% | 100% | 0% | 34% |

As shown in Table VIII above, exposure to the light generated by the exemplary wearable device resulted in an average increase in orgasm duration over all the subjects by 1.9 seconds or 34%.

Example 9: Evaluation of Satisfaction of Intercourse of Subjects

Prior to exposure to the light, the subjects were asked to provide their sexual satisfaction with their partner on a scale from 1 to 10 with 10 being the highest satisfaction. After completion of the Exposure Period as described in Example 1, the subjects were asked once again to provide their sexual satisfaction on the scale from 1 to 10. The results were recorded as provided in Table IX below.

TABLE IX

| | Results of the Evaluation of Example 9 | | | | | | | | | | |
|---|---|---|---|---|---|---|---|---|---|---|---|
| Subject | 1 | 2 | 3 | 4 | 5 | 6 | 7 | 8 | 9 | 10 | Avg. |
| Satisfaction of Intercourse prior to Exposure Period (Scale) | 9 | 4 | 5 | 7 | 5 | 6 | 7 | 5 | 6 | 8 | 6.2 |
| Satisfaction of Intercourse after Exposure Period (Scale) | 9 | 8 | 6 | 7 | 7 | 8 | 10 | 6 | 8 | 8 | 7.7 |
| Improvement (Scale) | 0 | 4 | 1 | 0 | 2 | 2 | 3 | 1 | 2 | 0 | 1.5 |
| Improvement (Percent) | 0% | 100% | 20% | 0% | 40% | 33% | 43% | 20% | 33% | 0% | 24% |

As shown in Table IX above, exposure to the light generated by the exemplary wearable device resulted in an average increase in intercourse satisfaction over all the subjects by 1.5 points or 24%.

Example 10: Evaluation of Sexual Frequency of Subjects

Prior to exposure to the light, the subjects were asked to provide the average number of acts of sexual intercourse with their partner ("Sexual Frequency") in a week. After completion of the Exposure Period as described in Example 1, the subjects were asked once again to provide their Sexual Frequency in a week. The results were recorded as provided in Table X below.

TABLE X

| | Results of the Evaluation of Example 10 | | | | | | | | | | |
|---|---|---|---|---|---|---|---|---|---|---|---|
| Subject | 1 | 2 | 3 | 4 | 5 | 6 | 7 | 8 | 9 | 10 | Avg. |
| Sexual Frequency prior to Exposure Period (Intercourse per Week) | 7 | 1 | 4 | 3 | 3 | 1 | 5 | 1 | 1 | 2 | 2.8 |
| Sexual Frequency after Exposure Period (Intercourse per Week) | 7 | 4 | 5 | 5 | 7 | 3 | 8 | 2 | 2 | 2 | 4.5 |
| Improvement (Intercourse per Week) | 0 | 3 | 1 | 2 | 4 | 2 | 3 | 1 | 1 | 0 | 1.7 |
| Improvement (Percent) | 0% | 300% | 25% | 67% | 133% | 200% | 60% | 100% | 100% | 0% | 61% |

As shown in Table X above, exposure to the light generated by the exemplary wearable device resulted in an average increase in sexual frequency over all the subjects by 1.7 points or 61%.

Example 11: Evaluation of Mood of Subjects

Prior to exposure to the light, the subjects were asked to provide their mood on a scale from 1 to 10 with 10 being the highest mood. After completion of the Exposure Period as described in Example 1, the subjects were asked once again to provide their mood on the scale from 1 to 10. The results were recorded as provided in Table XI below.

TABLE XI

Results of the Evaluation of Example 11

| Subject | 1 | 2 | 3 | 4 | 5 | 6 | 7 | 8 | 9 | 10 | Avg. |
|---|---|---|---|---|---|---|---|---|---|---|---|
| Mood prior to Exposure Period (Scale) | 9 | 8 | 3 | 3 | 2 | 8 | 6 | 5 | 2 | 5 | 5.1 |
| Mood after Exposure Period (Scale) | 9 | 9 | 7 | 5 | 8 | 8 | 9 | 5 | 5 | 5 | 7 |
| Improvement (Scale) | 0 | 5 | 1 | 1 | 4 | 2 | 3 | 0 | 0 | 0 | 1.6 |
| Improvement (Percent) | 0% | 167% | 14% | 17% | 100% | 33% | 50% | 0% | 0% | 0% | 26% |

As shown in Table XI above, exposure to the light generated by the exemplary wearable device resulted in an average improvement in mood over all the subjects by 1.6 points or 26%.

Example 12: Evaluation of Confidence of Subjects

Prior to exposure to the light, the subjects were asked to provide their confidence on a scale from 1 to 10 with 10 being the highest confidence. After completion of the Exposure Period as described in Example 1, the subjects were asked once again to provide their confidence on the scale from 1 to 10. The results were recorded as provided in Table XII below.

TABLE XII

Results of the Evaluation of Example 12

| Subject | 1 | 2 | 3 | 4 | 5 | 6 | 7 | 8 | 9 | 10 | Avg. |
|---|---|---|---|---|---|---|---|---|---|---|---|
| Confidence prior to Exposure Period (Scale) | 8 | 7 | 7 | 5 | 6 | 8 | 7 | 10 | 4 | 7 | 6.9 |
| Confidence after Exposure Period (Scale) | 9 | 9 | 8 | 5 | 9 | 8 | 9 | 10 | 6 | 7 | 8 |
| Improvement (Scale) | 1 | 2 | 1 | 0 | 3 | 0 | 2 | 0 | 2 | 0 | 1.1 |
| Improvement (Percent) | 13% | 29% | 14% | 0% | 50% | 0% | 29% | 0% | 50% | 0% | 16% |

As shown in Table XII above, exposure to the light generated by the exemplary wearable device resulted in an average increase in confidence over all the subjects by 1.1 points or 16%.

Example 13: Evaluation of Motivation Level of Subjects

Prior to exposure to the light, the subjects were asked to provide their motivation level on a scale from 1 to 10 with 10 being the highest motivation level. After completion of the Exposure Period as described in Example 1, the subjects were asked once again to provide their motivation level on the scale from 1 to 10. The results were recorded as provided in Table XIII below.

TABLE XIII

Results of the Evaluation of Example 13

| Subject | 1 | 2 | 3 | 4 | 5 | 6 | 7 | 8 | 9 | 10 | Avg. |
|---|---|---|---|---|---|---|---|---|---|---|---|
| Motivation Level prior to Exposure Period (Scale) | 7 | 7 | 7 | 5 | 3 | 7 | 7 | 8 | 5 | 6 | 6.2 |

TABLE XIII-continued

Results of the Evaluation of Example 13

| Subject | 1 | 2 | 3 | 4 | 5 | 6 | 7 | 8 | 9 | 10 | Avg. |
|---|---|---|---|---|---|---|---|---|---|---|---|
| Motivation Level after Exposure Period (Scale) | 9 | 8 | 7 | 5 | 9 | 8 | 9 | 8 | 5 | 6 | 7.4 |
| Improvement (Scale) | 2 | 1 | 0 | 0 | 6 | 1 | 2 | 0 | 0 | 0 | 1.2 |
| Improvement (Percent) | 29% | 14% | 0% | 0% | 200% | 14% | 29% | 0% | 0% | 0% | 19% |

As shown in Table XIII above, exposure to the light generated by the exemplary wearable device resulted in an average increase in motivation over all the subjects by 1.2 points or 19%.

Example 14: Evaluation of Aggressiveness of Subjects

Prior to exposure to the light, the subjects were asked to provide their aggressiveness on a scale from 1 to 10 with 10 being the highest aggressiveness. After completion of the Exposure Period as described in Example 1, the subjects were asked once again to provide their aggressiveness on the scale from 1 to 10. The results were recorded as provided in Table XIV below.

TABLE XIV

Results of the Evaluation of Example 14

| Subject | 1 | 2 | 3 | 4 | 5 | 6 | 7 | 8 | 9 | 10 | Avg. |
|---|---|---|---|---|---|---|---|---|---|---|---|
| Aggressiveness prior to Exposure Period (Scale) | 3 | 8 | 5 | 3 | 5 | 4 | 5 | 4 | 6 | 3 | 4.6 |
| Aggressiveness after Exposure Period (Scale) | 2 | 5 | 5 | 3 | 5 | 4 | 5 | 4 | 3 | 3 | 3.9 |
| Improvement (Scale) | −1 | −3 | 0 | 0 | 0 | 0 | 0 | 0 | −3 | 0 | −0.7 |
| Improvement (Percent) | −33% | −38% | 0% | 0% | 0% | 0% | 0% | 0% | −50% | 0% | −15% |

As shown in Table XIV above, exposure to the light generated by the exemplary wearable device resulted in an average decrease in aggressiveness over all the subjects by 0.7 points or 15%.

Example 15: Evaluation of Activity Level of Subjects

Prior to exposure to the light, the subjects were asked to provide their activity level on a scale from 1 to 10 with 10 being the highest activity level. After completion of the Exposure Period as described in Example 1, the subjects were asked once again to provide their activity level on the scale from 1 to 10. The results were recorded as provided in Table XV below.

TABLE XV

Results of the Evaluation of Example 15

| Subject | 1 | 2 | 3 | 4 | 5 | 6 | 7 | 8 | 9 | 10 | Avg. |
|---|---|---|---|---|---|---|---|---|---|---|---|
| Activity Level prior to Exposure Period (Scale) | 8 | 7 | 6 | 3 | 5 | 5 | 7 | 7 | 2 | 5 | 5.5 |

TABLE XV-continued

Results of the Evaluation of Example 15

| Subject | 1 | 2 | 3 | 4 | 5 | 6 | 7 | 8 | 9 | 10 | Avg. |
|---|---|---|---|---|---|---|---|---|---|---|---|
| Activity Level after Exposure Period (Scale) | 8 | 8 | 7 | 3 | 7 | 8 | 8 | 7 | 3 | 5 | 6.4 |
| Improvement (Scale) | 0 | 1 | 1 | 0 | 2 | 3 | 1 | 0 | 1 | 0 | 0.9 |
| Improvement (Percent) | 0% | 14% | 17% | 0% | 40% | 60% | 14% | 0% | 50% | 0% | 16% |

As shown in Table XV above, exposure to the light generated by the exemplary wearable device resulted in an average increase in activity level over all the subjects by 0.9 points or 16%.

Example 16: Evaluation of Endurance Level of Subjects

Prior to exposure to the light, the subjects were asked to provide their endurance level on a scale from 1 to 10 with 10 being the highest endurance level. After completion of the Exposure Period as described in Example 1, the subjects were asked once again to provide their endurance level on the scale from 1 to 10. The results were recorded as provided in Table XVI below.

TABLE XVI

Results of the Evaluation of Example 16

| Subject | 1 | 2 | 3 | 4 | 5 | 6 | 7 | 8 | 9 | 10 | Avg. |
|---|---|---|---|---|---|---|---|---|---|---|---|
| Endurance Level prior to Exposure Period (Scale) | 7 | 8 | 5 | 5 | 3 | 7 | 7 | 7 | 4 | 5 | 5.8 |
| Endurance Level after Exposure Period (Scale) | 9 | 9 | 5 | 5 | 9 | 8 | 8 | 8 | 4 | 5 | 7 |
| Improvement (Scale) | 2 | 1 | 0 | 0 | 6 | 1 | 1 | 1 | 0 | 0 | 1.2 |
| Improvement (Percent) | 29% | 13% | 0% | 0% | 200% | 14% | 14% | 14% | 0% | 0% | 21% |

As shown in Table XVI above, exposure to the light generated by the exemplary wearable device resulted in an average increase in endurance over all the subjects by 1.2 points or 21%.

Example 17: Evaluation of Strength Level of Subjects

Prior to exposure to the light, the subjects were asked to provide their strength level on a scale from 1 to 10 with 10 being the highest strength level. After completion of the Exposure Period as described in Example 1, the subjects were asked once again to provide their strength level on the scale from 1 to 10. The results were recorded as provided in Table XVII below.

TABLE XVII

Results of the Evaluation of Example 17

| Subject | 1 | 2 | 3 | 4 | 5 | 6 | 7 | 8 | 9 | 10 | Avg. |
|---|---|---|---|---|---|---|---|---|---|---|---|
| Strength Level prior to Exposure Period (Scale) | 7 | 8 | 5 | 4 | 3 | 5 | 5 | 7 | 3 | 6 | 5.3 |

TABLE XVII-continued

Results of the Evaluation of Example 17

| Subject | 1 | 2 | 3 | 4 | 5 | 6 | 7 | 8 | 9 | 10 | Avg. |
|---|---|---|---|---|---|---|---|---|---|---|---|
| Strength Level after Exposure Period (Scale) | 9 | 9 | 5 | 4 | 7 | 5 | 8 | 7 | 4 | 6 | 6.4 |
| Improvement (Scale) | 2 | 1 | 0 | 0 | 4 | 0 | 3 | 0 | 1 | 0 | 1.1 |
| Improvement (Percent) | 29% | 13% | 0% | 0% | 133% | 0% | 60% | 0% | 33% | 0% | 21% |

As shown in Table XVII above, exposure to the light generated by the exemplary wearable device resulted in an average increase in strength over all the subjects by 1.1 points or 21%.

Example 18: Evaluation of Appetite of Subjects

Prior to exposure to the light, the subjects were asked to provide their appetite on a scale from 1 to 10 with 10 being the highest appetite. After completion of the Exposure Period as described in Example 1, the subjects were asked once again to provide their appetite on the scale from 1 to 10. The results were recorded as provided in Table XVII below.

TABLE XVIII

Results of the Evaluation of Example 18

| Subject | 1 | 2 | 3 | 4 | 5 | 6 | 7 | 8 | 9 | 10 | Avg. |
|---|---|---|---|---|---|---|---|---|---|---|---|
| Appetite prior to Exposure Period (Scale) | 6 | 10 | 5 | 7 | 5 | 8 | 9 | 8 | 9 | 4 | 7.1 |
| Appetite after Exposure Period (Scale) | 6 | 8 | 3 | 6 | 5 | 5 | 5 | 8 | 7 | 4 | 5.7 |
| Improvement (Scale) | 0 | −2 | −2 | −1 | 0 | −3 | −4 | 0 | −2 | 0 | −1.4 |
| Improvement (Percent) | 0% | −20% | −40% | −14% | 0% | −38% | −44% | 0% | −22% | 0% | −20% |

As shown in Table XVIII above, exposure to the light generated by the exemplary wearable device resulted in an average decrease in appetite over all the subjects by 1.4 points or 10%.

Example 19: Evaluation of Testosterone Level of Subjects

Prior to exposure to the light, the subjects were assessed for their testosterone level in nanograms per deciliter (ng/dL). After completion of the Exposure Period as described in Example 1, the subjects were once again assessed for their testosterone level. The results were recorded as provided in Table XIX below.

TABLE XIX

Results of the Evaluation of Example 19

| Subject | 1 | 2 | 3 | 4 | 5 | 6 | 7 | 8 | 9 | 10 | Avg. |
|---|---|---|---|---|---|---|---|---|---|---|---|
| Testosterone Level prior to Exposure Period (ng/dL) | 378 | 566 | 516 | 228 | 336 | 640 | 636 | 324 | 337 | 547 | 450.8 |

TABLE XIX-continued

Results of the Evaluation of Example 19

| Subject | 1 | 2 | 3 | 4 | 5 | 6 | 7 | 8 | 9 | 10 | Avg. |
|---|---|---|---|---|---|---|---|---|---|---|---|
| Testosterone Level after Exposure Period (ng/dL) | 510 | 594 | 648 | 262 | 492 | 681 | 690 | 348 | 382 | 615 | 522.2 |
| Improvement (ng/dL) | 132 | 28 | 132 | 34 | 156 | 41 | 54 | 24 | 45 | 68 | 71.4 |
| Improvement (Percent) | 35% | 5% | 26% | 15% | 46% | 6% | 8% | 7% | 13% | 12% | 16% |

As shown in Table XIX above, exposure to the light generated by the exemplary wearable device resulted in an average increase in testosterone levels over all the subjects in an amount of 71.4 ng/dL or 16%.

Summary of Examples 1-19

As described in Examples 1-19, the exemplary wearable device was effective for improving several physical, physiological, and emotional characteristics and performance indicators of the subjects. While all improvements are surprising to the inventors, the improvements relating to aggressiveness, mood, sleep, and sexual functional are very unexpected.

With regard to aggressiveness, conventional testosterone treatments (e.g., supplementing with testosterone or related metabolites as an anabolic steroid) are well known to increase aggressiveness in many of its users. However, the exemplary wearable device did not increase aggressiveness in the subjects (see Example 14) while still increasing testosterone levels (see Example 19). In fact, some subjects experienced a decrease in aggressiveness after use of the exemplary wearable device (see Example 14).

With regard to mood, conventional testosterone treatments (e.g., supplementing with testosterone or related metabolites as an anabolic steroid or as an androgenic steroid) are not conclusively known to improve cognitive function or mood in subject (see e.g., Petering R C, Brooks N A. Testosterone Therapy: Review of Clinical Applications. Am Fam Physician. 2017 Oct. 1; 96(7):441-449. Erratum in: Am Fam Physician. 2019 Oct. 1; 100(7):393, which is hereby incorporated by reference in its entirety). However, the exemplary wearable device increased cognitive function and mood of the subjects (see Examples 1, 10, 11, 12, and 14).

With regard to sleep, conventional testosterone treatments (e.g., supplementing with testosterone or related metabolites as an anabolic steroid or as an androgenic steroid) are known to negatively impact sleep (see e.g., Liu P Y, Yee B, Wishart S M, Jimenez M, Jung D G, Grunstein R R, Handelsman D J. The short-term effects of high-dose testosterone on sleep, breathing, and function in older men. J Clin Endocrinol Metab. 2003 August; 88(8):3605-13. doi: 10.1210/j c.2003-030236, which is hereby incorporated by reference in its entirety). However, the exemplary wearable device increased sleep duration and decreased sleep onset of the subjects (see Examples 2 and 3).

With regard to sexual functional, conventional testosterone treatments (e.g., supplementing with testosterone or related metabolites as an anabolic steroid or as an androgenic steroid) are not conclusively known to improve sexual function of subject (see e.g., Petering R C, Brooks N A. Testosterone Therapy: Review of Clinical Applications. Am Fam Physician. 2017 Oct. 1; 96(7):441-449. Erratum in: Am Fam Physician. 2019 Oct. 1; 100(7):393). However, the exemplary wearable device increased libido, intercourse duration, hardness, orgasm duration, intercourse satisfaction, and intercourse frequency of the subjects (see Examples 4-9).

Without being bound by theory, the inventors contemplate that the increase of endogenous testosterone resulting from in vivo testosterone production as promoted by the exemplary wearable device provided the subjects testosterone kinetics that were superior to the testosterone kinetics resulting from testosterone supplementation (e.g., as an anabolic steroid or as an androgenic steroid). Moreover, it is contemplated that the testosterone generation upon illumination of the photoresponsive tissue is not subject to first-pass liver metabolism and as such may provide a distinct activity profile (due to the presence or lack of one or more metabolites) than orally administered testosterone and/or injectable forms of testosterone.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. The recitation of ranges of values herein is merely intended to serve as a shorthand method of referring individually to each separate value falling within the range. Unless otherwise indicated herein, each individual value is incorporated into the specification as if it were individually recited herein.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). It should further be noted that the terms "prognosing" or "predicting" a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

What is claimed is:

1. A method of effecting photobiomodulation in a male individual, comprising:
    attaching or causing to attach a wearable photobiomodulation device to the genital area of the male individual such that the wearable photobiomodulation device delivers for a predetermined time a 5-50 mJ/cm² dose of light to a photoresponsive portion of the male individual, which is scrotal and underlying testicular tissue;
    wherein the dose of light delivered to the male individual is sufficient to increase endogenous testosterone in the male individual by at least 5% but not increase aggressiveness in the male individual, and
    wherein the wearable photobiomodulation device comprises:
        a molded polymeric shell having an inside surface and an outside surface; and
        an illumination component coupled to the shell and configured to deliver the dose of light to the photoresponsive portion of a body of the male individual wearing the device, wherein:
            the inside surface has a shape that contours the photoresponsive portion of the body;
            the illumination component is coupled to the inside surface of the molded polymeric shell;
            the illumination component comprises one or more laser diodes or light emitting diodes emitting red light and/or infrared light;
            the red light and/or infrared light has a wavelength of 660 nm or 880 nm; and
            the illumination component is configured and coupled to the inside surface of the molded polymeric shell such that the light is delivered to the photoresponsive portion of the body over a distance of no more than 5 cm.

2. The method of claim 1, wherein the wearable photobiomodulation device is attached to the individual and turned on for a time between 10 and 60 minutes while delivering the dose of light.

3. The method of claim 1, wherein the dose is delivered to a target tissue area of about 100-200 cm².

4. The method of claim 1, wherein the dose of light is administered no more than 3 hours prior to bedtime of the individual.

5. The method of claim 4, wherein the red light and/or infrared light has a wavelength of 660 nm and the dose of light is sufficient to increase the endogenous testosterone in the individual by 5-46%.

6. The method of claim 5, comprising attaching the wearable photobiomodulation device to the genital area of the individual.

7. The method of claim 1, wherein the red light and/or infrared light has a wavelength of 660 nm and the dose of light is sufficient to increase the endogenous testosterone in the individual by 5-46%.

8. The method of claim 7, comprising attaching the wearable photobiomodulation device to the genital area of the individual.

9. The method of claim 1, wherein the red light and/or infrared light has a wavelength of 880 nm.

* * * * *